(12) United States Patent
Bodenmiller et al.

(10) Patent No.: US 9,739,765 B2
(45) Date of Patent: Aug. 22, 2017

(54) METAL-BASED COVALENT VIABILITY REAGENT FOR SINGLE CELL ANALYSIS

(71) Applicant: The Board of Trustees of the Leland Stanford Junior University, Palo Alto, CA (US)

(72) Inventors: Bernd Bodenmiller, Zurich (CH); Erin F. Simonds, Stanford, CA (US); Harris G. Fienberg, Stanford, CA (US); Garry P. Nolan, San Francisco, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 329 days.

(21) Appl. No.: 14/268,997

(22) Filed: May 2, 2014

(65) Prior Publication Data

US 2014/0329272 A1 Nov. 6, 2014

Related U.S. Application Data

(60) Provisional application No. 61/818,725, filed on May 2, 2013.

(51) Int. Cl.
*C12Q 1/04* (2006.01)
*G01N 33/50* (2006.01)

(52) U.S. Cl.
CPC .................. *G01N 33/5005* (2013.01)

(58) Field of Classification Search
CPC .................................................. G01N 33/5005
See application file for complete search history.

(56) References Cited

U.S. PATENT DOCUMENTS

2012/0178183 A1* 7/2012 Nolan ................. B82Y 5/00
436/501

OTHER PUBLICATIONS

Webpage from Excyte expert cytometer https://expertcytometry.com/cytof/ downlowded Jun. 13, 2016.*
Enzweiler et al. Analyst (1995) 120: 1391-1396.*
Schutz et al. J. Immunol. Methods (2009) 344: 98-108.*
Bendall; et al., "Single-Cell Mass Cytometry of Differential Immune and Drug Responses Across a Human Hematopoeietic Continuum", Science (May 2011), 332(6030):687-96.
Dattelbaum; et al., "Synthesis and Characterization of Sulfhydryl-Reactive Rhenium Metal-Ligand Complex", Bioconjug. Chem. (Jul.-Aug. 2000), 11(4):553-6.
Fienberg; et al., "A platinum-based covalent viability reagent for single-cell mass cytometry", Cytomtry A. (Jun. 2012), 81(6):467-75.
Majonis; et al., "Curious results with palladium- and platinum-carry polymers in mass cytometry bioassays and an unexpected application as a dead cell stain", Biomacromolecules (Nov. 2011), 12(11):3997-4010.
Ornatsky; et al., "Development of analytical methods for multiplex bio-assay with inductively coupled plasma mass spectrometry", J. Anal. At Spectrom. (2008), 23(4):463-469.

* cited by examiner

*Primary Examiner* — Susan Hanley
(74) *Attorney, Agent, or Firm* — Pamela J. Sherwood; Bozicevic, Field & Francis LLP (57) ABSTRACT

The present invention provides a robust viability stain for methods utilizing elemental analysis. A population of cells is contacted with an effective dose of a non-chelated biomacromolecule-reactive metal derivative, which selectively crosses the plasma membrane of non-viable cells, and which covalently modifies a biological macromolecule within the cell, for a period of time sufficient to permit entry into non-viable cells. The population of cells is then washed free of unbound viability reagent; and the presence of the metal within the cells is detected, wherein non-viable cells are selectively labeled with the viability reagent.

14 Claims, 5 Drawing Sheets

METAL-BASED COVALENT VIABILITY REAGENT FOR SINGLE CELL ANALYSIS

FEDERALLY SPONSORED RESEARCH AND DEVELOPMENT

This invention was made with Government support under contracts AI057229, CA034233, CA130826, and CA149145 awarded by the National Institutes of Health. The Government has certain rights in the invention.

BACKGROUND OF THE INVENTION

Traditional flow cytometry allows for fluorescently labeled live cells, fixed cells, beads, or objects to be individually distinguished and separated using cytometric sorting technology based on their fluorescent and light scatter characteristics. This approach is particularly advantageous because it allows for further functional or analytical characterization of individually purified cells on a phenotypic basis.

An essential phenotype measured in most cell analysis experiments is cell viability, as dead cells can easily distort the analyzed phenotypes. Cell viability is typically determined by molecules that cannot pass the intact membrane of a live cell, but which enter the cytoplasm and nucleus of dead cells. Examples include propidium iodide and ethidium monoazide, which intercalate or covalently bind to DNA. Alternatively, fluorescently labeled affinity binders specific for cell death markers, such as cleaved Caspase 3, cleaved Parp or Annexin V can be used for this purpose. As a result live and dead cells can be easily distinguished based on the fluorescence intensity of the fluorophore used for the viability stain.

Elemental mass spectrometry-based flow cytometry (mass cytometry) is a recently developed method to characterize single cells or particles via the replacement of fluorochrome-labeled binding reagents with elemental metal isotope-labeled binding reagents. Because there are many stable metal isotopes available, and little overlap between measurement channels, dozens of molecules (parameters) can be readily measured. An example of a mass cytometer used to read the metal tags is an inductively-coupled plasma mass spectrometer (ICP-MS), which in its current configuration allows analysis of up to 100 isotopes from the mass 100-200 and therefore molecules simultaneously[2]. In a typical workflow (similar to fluorescence based cytometry), cells are first incubated with antibodies/affinity binders conjugated to pure isotopes and subsequently the cell suspension is injected as a single cell stream into the mass cytometer. Single cell droplets are generated via nebulization and are carried by an argon gas stream into a ~7500 degrees Kelvin plasma where each single cell is completely atomized and ionized. Thereby generated metal ions are then directed into a time-of-flight (TOF) mass spectrometer and the mass over charge ratio and number of metal ions is measured per cell and thereby the abundance of the target epitope/molecules.

The value of this mass cytometry-based technique, including the routine measurement of up to 33 parameters, has recently been documented. One limitation, however, is that no robust method for an accurate discrimination of live and dead cells in a given sample exists. Conventional methods developed for flow cytometry methods rely on metal labeled DNA intercalators, however, as these compounds are not covalently bound to the cell, they are easily washed out in subsequent sample processing steps, making the reliable determination of a cells live/dead status very difficult.

Consequently, many analyses performed with mass cytometry fall short of yielding an accurate picture of a phenotypic signature; and it is not possible to determine the impact of the dead cells on the performed experiment. For example, dead cells can exhibit false-negative or false-positive staining for various surface and intracellular targets. A viability assay is needed to positively identify these dead and resolve the heterogeneous staining. Additionally, quantification of dead cells is helpful in measuring the efficacy of in vitro drug treatments meant to kill cells (i.e. chemotherapeutic agents). Therefore, there is great value in a method that overcomes the lack of a live/dead cellular viability assay. The present invention addresses this need.

Publications

Fienberg et al. (2012) Cytometry A 81(6):467-75, entitled "A platinum-based covalent viability reagent for single-cell mass cytometry." Majonis et al. (2011) Biomacromolecules 12(11):3997-4010, entitled "Curious results with palladium- and platinum-carrying polymers in mass cytometry bioassays and an unexpected application as a dead cell stain." Bendall et al. (2011) Science 332(6030):687-96, entitled "Single-cell mass cytometry of differential immune and drug responses across a human hematopoietic continuum." Ornatsky et al. (2008) J Anal At Spectrom 23(4):463-469, entitled "Development of analytical methods for multiplex bio-assay with inductively coupled plasma mass spectrometry." Rieger et al. (2010) J Immunol Methods. 358(1-2): 81-92, entitled "Conventional apoptosis assays using propidium iodide generate a significant number of false positives that prevent accurate assessment of cell death." Stocks (2004) Cytometry A. 61(2):189-95, entitled "Mechanism and use of the commercially available viability stain, BacLight." Berber et al. (1999) Cytometry. 36(4):349-54, entitled "Fluoro-Gold: An alternative viability stain for multicolor flow cytometric analysis."

SUMMARY OF THE INVENTION

The present invention provides a robust viability stain for methods utilizing elemental analysis. By accurately labeling dead cells in a heterogeneous mixture, researchers can more accurately quantify cellular markers that are relevant in clinical and pharmaceutical analyses. In the methods of the invention, a population of cells is contacted with an effective dose of a non-chelated biomacromolecule-reactive metal derivative (referred to herein as a viability reagent), which selectively crosses the plasma membrane of non-viable cells, and which covalently modifies a biological macromolecule within the cell, for a period of time sufficient to permit entry into non-viable cells. The population of cells is then washed free of unbound viability reagent; and the presence of the metal from the reagent within the cells is detected, wherein non-viable cells are selectively labeled with the viability reagent. In one embodiment, the metal is platinum, and in certain such embodiments the viability reagent is cisplatin.

An advantage of the methods of the invention is the covalent binding of the viability reagent to biological macromolecules. As result, the viability reagent is very stable and does not "wash out" during processing. In some embodiments of the invention, additional steps are performed to detect the presence of analytes in the cell. Such additional steps may comprise, without limitation, cell permeabilization steps for intracellular staining protocols.

Elemental mass spectrometry-based detection can be used for the detection of the viability reagent metal in cells. In some embodiments the metal is selected from cadmium, renium, ruthenium, rhodium, palladium, silver, osmium, iridium, platinum, and gold. In some embodiments the metal is selected from renium, mercury, cadmium, bismuth, lead, tin, and antimony. In some specific embodiments the metal is platinum. The metal in the viability reagent can be a mixture of isotopes, e.g. naturally occurring platinum, or platinum that is artificially enriched for an isotope. Labeled cells are introduced into an analyzer, e.g. a mass cytometer, atomic mass spectrometer (ICP-MS), etc., where they are atomized and ionized. The ions are then subjected to elemental analysis, which identifies and measures the abundance of the metal from the reagent.

Other features and advantages of the present invention will become apparent from the following detailed description. It should be understood, however, that the detailed description and the specific preferred embodiments of the invention are given by way of illustration only, since various changes and modifications within the spirit and scope of the invention will become apparent to those skilled in the art from this detailed description.

DEFINITIONS

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention. Accordingly, the terms defined immediately below are more fully defined by reference to the specification as a whole.

A non-chelated biomacromolecule-reactive metal derivative, which may be referred to herein as the "metal derivative", or a "viability reagent", useful in the methods of the invention has the properties of (a) selectively crossing the plasma membrane when a cell is compromised, i.e. non-viable; and (b) covalently modifying a biological macromolecule within the cell. The metal derivative may, for example, react with protein nucleophiles such as R—SH, R—S—$CH_3$ or R—$NH_2$ to form covalent Pt—S or Pt—N bonds.

Exemplary metals include cadmium, renium, ruthenium, rhodium, palladium, silver, osmium, iridium, platinum, gold, renium, mercury, cadmium, bismuth, lead, tin, and antimony. For example, see Dattelbaum et al. (2000) Bioconjugate Chem. 11, 533-536 for a description of the sulfhydryl-reactive rhenium metal-ligand complex, Re(phen-IA)-$(CO)_3$Cl, herein specifically incorporated by reference).

In some embodiments the metal is platinum. Exemplary platinum derivatives include, without limitation, cisplatin, carboplatin, oxaliplatin, nedaplatin, lobaplatin, heptaplatin, satraplatin, picoplatin, prolindac, lipoplatin, JM-11, NSC 170898, ormaplatin, sebriplatin, enloplatin, zeniplatin, spiroplatin, cycloplatam, miboplatin, iproplatin, TRK-710, SPI-77, aroplatin, BBR3464, etc. In some embodiments the platinum derivative is cisplatin, [Pt$(NH_3)_2$Cl].

The platinum derivative is added to a cell population for a period of time sufficient to allow crossing of the cell membrane, which period of time may be a pulse of at from up to about 1 minute to about 1 hour, from up to about 1 minute to about 30 minutes, from up to about 1 minute to about 10 minutes, from up to about 1 minute to about 5 minutes, and may be from about 1 to 10 minutes duration. The cell population is washed of free platinum derivative following the pulse.

An effective dose of the viability reagent is the dose required to selectively label non-viable cells over viable cells, and may be from up to about 1 μM to about 500 μM; from up to about 1 μM to about 250 μm; from up to about 1 μM to about 100 μM; from up to about 1 μM to about 50 μM; from up to about 10 μM to about 50 μM; and may be around about 10 to 25 μM of the viability reagent.

The metal in the viability reagent may be a naturally occurring mixture of isotopes, or may be enriched for an isotope of interest. Where the metal is platinum; naturally occurring platinum contains six stable isotopes (190, 192, 194, 195, 196, 198), any of which may be enriched. For determination of viability, it is only necessary to measure one isotope, e.g. the most abundant isotope ($Pt^{195}$). However, the channels occupied by the non-detected isotopes could be used for additional markers, thus providing a benefit for viability reagents enriched for an isotope of interest.

Cellular death, or non-viability, as used herein is given its common meaning and may refer to any kind of cellular death, including apoptosis, autophagy cell death, necrosis, anoikis, excitotoxicity, wallerian degeneration, cornification, programmed cell death, caspase-independent apoptosis, any other form of cell death. In addition, all stages of the cell death, individually or all at once, can be detected.

Selective labeling. The viability reagent of the invention selectively stains non-viable cells, as their cell membrane is compromised and permits entry of the reagent into the cell. For analytic purposes, e.g. to gate out the dead cells, the cells that are positive for the presence of viability reagent are registered as non-viable, and the cells that are negative or low for the presence of viability reagent are registered as viable. The absolute level of metal present in cells may vary, but there will be a difference between the viable and non-viable cells.

In order to normalize the distribution to a control, each cell can be recorded as a data point having a particular intensity of staining. These data points may be displayed according to a log scale, where the unit of measure is arbitrary intensity. In one example, the cells designated as "positive" have about 1 log, 2 log, 3 logs or more signal intensity than the cells having the lowest level of staining, designated as "negative". In other embodiments cells designated as positive have about 2-fold, 5-fold or more signal intensity relative to cells designated as negative. When displayed in this manner, it is clear that there is a distinct difference between positive and negative cells as shown, for example, in FIG. 2. The positive cells can be 2-fold to 10,000 fold more intensity in platinum signal.

Cells. Cells for use in the assays of the invention can be an organism, a single cell type derived from an organism, or can be a mixture of cell types. Included are naturally occurring cells and cell populations, genetically engineered cell lines, cells derived from transgenic animals, etc. Virtually any cell type and size can be accommodated. Suitable cells include bacterial, fungal, plant and animal cells. In one embodiment of the invention, the cells are mammalian cells, e.g. complex cell populations such as naturally occurring tissues, for example blood, liver, pancreas, neural tissue, bone marrow, skin, and the like. In another embodiment of the invention, the cells are from diseased origin, such as solid tumors or leukemia. Some tissues may be disrupted into a monodisperse suspension if the cells are not yet already in suspension. Alternatively, the cells may be a cultured population, e.g. a culture derived from a complex population, a culture derived from a single cell type where the cells have differentiated into multiple lineages, or where the cells are responding differentially to stimulus, and the like.

Cell types that can find use in the subject invention include stem and progenitor cells, e.g. embryonic stem cells, hematopoietic stem cells, mesenchymal stem cells, neural crest cells, etc., endothelial cells, muscle cells, myocardial, smooth and skeletal muscle cells, mesenchymal cells, epithelial cells; hematopoietic cells, such as lymphocytes, including T-cells, such as Th1 T cells, Th2 T cells, Th0 T cells, cytotoxic T cells; B cells, pre-B cells, etc.; monocytes; dendritic cells; neutrophils; and macrophages; natural killer cells; mast cells; etc.; adipocytes, cells involved with particular organs, such as thymus, endocrine glands, pancreas, brain, such as neurons, glia, astrocytes, dendrocytes, etc. and genetically modified cells thereof. Hematopoietic cells may be associated with inflammatory processes, autoimmune diseases, etc., endothelial cells, smooth muscle cells, myocardial cells, etc. may be associated with cardiovascular diseases; almost any type of cell may be associated with neoplasias, such as sarcomas, carcinomas and lymphomas; liver diseases with hepatic cells; kidney diseases with kidney cells; etc.

The cells may also be transformed or neoplastic cells of different types, e.g. carcinomas of different cell origins, lymphomas of different cell types, etc. The American Type Culture Collection (Manassas, Va.) has collected and makes available over 4,000 cell lines from over 150 different species, over 950 cancer cell lines including 700 human cancer cell lines. The National Cancer Institute has compiled clinical, biochemical and molecular data from a large panel of human tumor cell lines, these are available from ATCC or the NCI (Phelps et al. (1996) *Journal of Cellular Biochemistry* Supplement 24:32-91). Included are different cell lines derived spontaneously, or selected for desired growth or response characteristics from an individual cell line; and may include multiple cell lines derived from a similar tumor type but from distinct patients or sites.

Cells may be non-adherent, e.g. blood cells including monocytes, T cells, B-cells; tumor cells, etc., or adherent cells, e.g. epithelial cells, endothelial cells, neural cells, etc. In order to profile adherent cells, they must be dissociated from the substrate that they are adhered to, and from other cells, in a manner that maintains their ability to recognize and bind to probe molecules.

Such cells can be acquired from an individual using, e.g., a draw, a lavage, a wash, surgical dissection etc., from a variety of tissues, e.g., blood, marrow, a solid tissue (e.g., a solid tumor), ascites, by a variety of techniques that are known in the art. Cells may be obtained from fixed or unfixed, fresh or frozen, whole or disaggregated samples. Disaggregation of tissue may occur either mechanically or enzymatically using known techniques.

Various methods and devices exist for pre-separating component parts of the sample. These methods include filters, centrifuges, chromatographs, and other well-known fluid separation methods; gross separation using columns, centrifuges, filters, separation by killing of unwanted cells, separation with fluorescence activated cell sorters, separation by directly or indirectly binding cells to a ligand immobilized on a physical support, such as panning techniques, separation by column immunoadsorption, and separation using magnetic immunobeads.

Analysis methods in which the covalent platinum labeling of non-viable cells by the methods of the invention find use include any method of cell-specific analysis in which markers are detected, and in which the presence of a metal is determined by elemental analysis. Such methods include, without limitation, inductively coupled plasma mass spectrometry, secondary ion mass spectrometry; thermal ionization mass spectrometry, atomic absorption mass spectrometry, and which may be combined with traditional fluorescent flow cytometry. Sample acquisition methods include: solution-based acquisition, particle-based acquisition, and ablation-based acquisition.

As used herein, the term "elemental analysis" refers to a method by which the presence and/or abundance of elements of a sample are evaluated. "Capacitively coupled plasma" (CCP) means a source of ionization in which a plasma is established by capacitive coupling of radiofrequency energy at atmospheric pressure or at a reduced pressure (typically between 1 and 500 Torr) in a graphite or quartz tube. The term "inductively coupled plasma" (ICP) means a source of atomization and ionization in which a plasma is established in an inert gas (usually argon) by the inductive coupling of radiofrequency energy. The frequency of excitation force is in the MHz range. The term "plasma source" means a source of atoms or atomic ions comprising a hot gas (usually argon) in which there are approximately equal numbers of electrons and ions, and in which the Debye length is small relative to the dimensions of the source. The term "flow cell" refers to a conduit in which particles flow, in a medium, one by one in single file. The term "a diverter" refers to a branch of a flow cell in which particles can be separated from other components passing through the flow cell. "Laser ablation" means a source of combusted material liberated from an otherwise intact surface by exposure to laser radiation, optionally used in conjunction with microscopy to preserve spatial information. "Mass spectrometer" means an instrument for producing ions in a gas and analyzing them according to their mass/charge ratio. "Microwave induced plasma" (MIP) means a source of atomization and ionization in which a plasma is established in an inert gas (typically nitrogen, argon or helium) by the coupling of microwave energy. The frequency of excitation force is in the GHz range. "Glow discharge" (GD) means a source of ionization in which a discharge is established in a low pressure gas (typically between 0.01 and 10 Torr), typically argon, nitrogen or air, by a direct current (or less commonly radiofrequency) potential between electrodes. "Graphite furnace" means a spectrometer system that includes a vaporization and atomization source comprised of a heated graphite tube. Spectroscopic detection of elements within the furnace may be performed by optical absorption or emission, or the sample may be transported from the furnace to a plasma source (e.g. inductively coupled plasma) for excitation and determination by optical or mass spectrometry.

In some embodiments the methods for analysis utilize ICP-MS. In some embodiments the ICP-MS is performed with solution analysis, for example ELAN DRC II, Perkin-Elmer. In other embodiments the analysis is performed with a mass cytometer (e.g. CyTOF, DVS Sciences), which uses a nebulizer to administer a suspension of cells, beads, or other particles in a single-particle stream to an ICP-MS chamber, thereby yielding single particle/cell data similar to a flow cytometer. Alternatively the analysis is performed by an elemental analysis-driven imaging system (e.g. laser ablation ICP-MS). Devices for such analytic methods are known in the art.

The term "flow cytometry" as used herein refers to a method and a process whereby cells within a sample can be detected and identified when transversing past a detector within an apparatus containing a detecting source and a flowing apparatus.

The term "fluorescently activated cell sorting assay" (FACS) as used herein refers to any assay suitable for use in cell sorting techniques (e.g., flow cytometry) that employs detection of fluorescent signals.

The methods of the invention are usually, although not necessarily, combined with an analysis of analytes present on or in the cells. As used herein, analytes refers to quantifiable components of cells or biological material, particularly components that can be accurately measured. An analyte can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. Some variability may be expected and a range of values may be obtained using standard statistical methods with a common statistical method used to provide single values.

Analytes of interest include cytoplasmic, cell surface or secreted biomolecules, frequently biopolymers, e.g. polypeptides, polysaccharides, polynucleotides, lipids, etc. In some embodiments, analytes include specific epitopes. Epitopes are frequently identified using specific monoclonal antibodies or receptor probes. In some cases the molecular entities comprising the epitope are from two or more substances and comprise a defined structure; examples include combinatorially determined epitopes associated with heterodimeric proteins. An analyte may be detection of a specifically modified protein or oligosaccharide, e.g. a phosphorylated protein, such as a STAT transcriptional protein; or sulfated oligosaccharide, or such as the carbohydrate structure Sialyl Lewis x, a selectin ligand. The presence of the active conformation of a receptor may comprise one analyte while an inactive conformation of a receptor may comprise another, e.g. the active and inactive forms of heterodimeric integrin.

Analytes of interest include biological molecules in a variety of spatial configurations, on a variety of substrates, and in a variety of degraded states. An analyte may be a naturally occurring protein in its native conformation or chemically altered, denatured state. An analyte may be affixed to the cell in its native orientation, or it may be adhered to a variety of substrates, including synthetic substrates e.g. glass, plastic, or metal. An analyte may be affixed to planar substrates or bead-like substrates in a suspension. An analyte may be affixed to a substrate in a particular orientation by a second binding reagent, such as an antibody, as in the case of a sandwich ELISA.

Analytes of interest include polypeptides, and the epitope that is being quantitated by be a primary amino acid epitope, an epitope formed by protein secondary or tertiary structure, an epitope formed by two or more interacting polypeptides, or an epitope that results from posttranslational modification of a polypeptide.

Among the post-translational modifications that can be probed, are protein specific glycoslyation. Membrane associated carbohydrate is exclusively in the form of oligosaccharides covalently attached to proteins forming glycoproteins, and to a lesser extent covalently attached to lipid forming the glycolipids. Many proteins are modified at their N-termini following synthesis; in most cases the initiator methionine is hydrolyzed and an acetyl group is added to the new N-terminal amino acid. Post-translational methylation occurs at lysine residues in some proteins. Post-translational phosphorylation is one of the most common protein modifications that occurs in animal cells, often as a transient mechanism to regulate the biological activity of a protein. In animal cells serine, threonine and tyrosine are the amino acids subject to phosphorylation. Sulfate modification of proteins occurs at tyrosine residues such as in fibrinogen and in some secreted proteins. Prenylation refers to the addition of the 15 carbon farnesyl group or the 20 carbon geranylgeranyl group to acceptor proteins, both of which are isoprenoid compounds derived from the cholesterol biosynthetic pathway. Modifications of proteins that depend upon vitamin C as a cofactor include proline and lysine hydroxylations and carboxy terminal amidation. Vitamin K is a cofactor in the carboxylation of glutamic acid residues that results in the formation of a γ-carboxyglutamate (gamma-carboxyglutamate), referred to as a gla residue.

The term "specific binding member" as used herein refers to a member of a specific binding pair, i.e. two molecules, usually two different molecules, where one of the molecules through chemical or physical means specifically binds to the other molecule. For the purposes of the present invention, one of the molecules is an analyte as defined above, and generally the specific binding member is labeled for detection of fluorescence or elemental analysis, as known in the art.

The complementary members of a specific binding pair are sometimes referred to as a ligand and receptor; or receptor and counter-receptor. Specific binding indicates that the agent can distinguish a target antigen, or epitope within it, from other non-target antigens. It is specific in the sense that it can be used to detect a target antigen above background noise ("non-specific binding"). For example, a specific binding partner can detect a specific sequence or a topological conformation. A specific sequence can be a defined order of amino acids or a defined chemical moiety (e.g., where an antibody recognizes a phosphotyrosine or a particular carbohydrate configuration, etc.) which occurs in the target antigen. The term "antigen" is issued broadly, to indicate any agent which elicits an immune response in the body. An antigen can have one or more epitopes.

Binding pairs of interest include antigen and antibody specific binding pairs, complementary nucleic acids, peptide-MHC-antigen complexes and T cell receptor pairs, biotin and avidin or streptavidin; carbohydrates and lectins; complementary nucleotide sequences; peptide ligands and receptor; effector and receptor molecules; hormones and hormone binding protein; enzyme cofactors and enzymes; enzyme inhibitors and enzymes; and the like. The specific binding pairs may include analogs, derivatives and fragments of the original specific binding member. For example, an antibody directed to a protein antigen may also recognize peptide fragments, chemically synthesized peptidomimetics, labeled protein, derivatized protein, etc. so long as an epitope is present.

Immunological specific binding pairs include antigens and antigen specific antibodies; and T cell antigen receptors, and their cognate MHC-peptide conjugates. Suitable antigens may be haptens, proteins, peptides, carbohydrates, etc. Recombinant DNA methods or peptide synthesis may be used to produce chimeric, truncated, or single chain analogs of either member of the binding pair, where chimeric proteins may provide mixture(s) or fragment(s) thereof, or a mixture of an antibody and other specific binding members. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

A nucleic acid based binding partner such as an oligonucleotide can be used to recognize and bind DNA or RNA based analytes. The term "polynucleotide" as used herein may refer to peptide nucleic acids, locked nucleic acids, modified nucleic acids, and the like as known in the art. The polynucleotide can be DNA, RNA, LNA or PNA, although it is not so limited. It can also be a combination of one or more of these elements and/or can comprise other nucleic acid mimics.

Binding partners can be primary or secondary. Primary binding partners are those bound to the analyte of interest. Secondary binding partners are those that bind to the primary binding partner.

DETAILED DESCRIPTION OF THE EMBODIMENTS

Methods are provided for labeling cells according to their viability. A population of cells, which may be naturally occurring cells and cell populations, genetically engineered cell lines, cells derived from transgenic animals, etc. of any cell type and size, including bacterial, fungal, plant and animal cells is contacted with an effective dose of a non-chelated biomacromolecule-reactive metal derivative (referred to herein as a viability reagent), which selectively crosses the plasma membrane of non-viable cells, and which covalently modifies a biological macromolecule within the cell, for a period of time sufficient to permit entry into non-viable cells. The population of cells is then washed free of unbound viability reagent.

The viability labeling may be performed before, during or after optional labeling of the cells for additional analytes of interest. In such methods, the cell population is contacted with labeled probe(s) specific for one or more analytes of interest, and incubated for a period of time sufficient to bind the available analyte. The incubation will usually be at least about 30 seconds and usually less than about 24 hours, for example from about 1 to 10 minutes, from about 2 to 5 minutes, and the like. It is desirable to have a sufficient concentration of probe in the reaction mixture so that the efficiency of detection is not limited by lack of probe. The appropriate concentration can be determined by titration. Labeling can be direct or indirect, and include all labels known and used in the art, e.g. fluorescent, elemental, enzyme, etc. Where the labeling is indirect, a second stage probe or label can be used, by washing and resuspending in medium prior to incubation with the second stage probes.

Analytes of interest may be located on the cell surface, or may be located in the cytoplasm or nucleus of the cell. For such intracellular labeling it is generally desirable to fix and permeabilize the cells. Where fixation and permeabilization are included, the viability stain will be performed in a prior step.

For example, where transient signaling pathways are being analyzed, it is desirable to fix the cells at the desired timepoint, then permeabilize to allow the probes access to the intracellular environment. Various fixatives are known in the art, including formaldehyde, paraformaldehyde, formaldehyde/acetone, methanol/acetone, etc. Paraformaldehyde used at a final concentration of about 1 to 2% has been found to be a good cross-linking fixative. Permeabilizing agents are known in the art, and include mild detergents, such as Triton X-100, NP-40, saponin, etc.; methanol, and the like. It may also be desirable to label cells with a positive heavy metal control, e.g. a DNA intercalator labeled with a heavy metal, e.g. iridium, etc.

The cells are washed of unbound probe using any suitable method known in the art. For example cells or beads may be pelleted and washed in PBS or normal saline. Cells may be resuspended for analysis in any suitable buffer.

The presence of platinum, and optionally other elemental labels within a cell is detected by elemental mass spectrometry-based detection. Labeled cells are introduced into a detector, e.g. a mass cytometer, atomic mass spectrometer (ICP-MS), etc., where they are atomized and ionized. The particles or solution are then subjected to elemental analysis, which identifies and measures the abundance of the platinum, and optionally other labels.

In one embodiment analysis is performed on a mass cytometer, in which cells are introduced into a fluidic system and introduced into the mass cytometer one cell at a time. In one embodiment, cells are carried in a liquid suspension and sprayed into a plasma source by means of a nebulizer. In another embodiment, the cells may be hydrodynamically focused one cell at a time through a flow cell using a sheath fluid. In particular embodiments, the cells may be compartmentalized in the flow cell by introduction of an immiscible barrier, e.g., using a gas (e.g., air or nitrogen) or oil, such that the cell is physically separated from other cells that are passing through the flow cell. The cells may be compartmentalized prior to or during introduction of the cell into the flow cell by introducing an immiscible material (e.g., air or oil) into the flow path.

The general principles of mass cytometry, including methods by which single cell suspensions can be made, methods by which cells can be labeled, methods for atomizing particles and methods for performing elemental analysis on particles, as well as hardware that can be employed in mass cytometry, including flow cells, ionization chambers, reagents, mass spectrometers and computer control systems are known and are reviewed in a variety of publications including, but not limited to Bandura et al Analytical Chemistry 2009 81 6813-6822), Tanner et al (Pure Appl. Chem 2008 80: 2627-2641), U.S. Pat. No. 7,479,630 (Method and apparatus for flow cytometry linked with elemental analysis) and U.S. Pat. No. 7,135,296 (Elemental analysis of tagged biologically active materials); and published U.S. patent application 20080046194, for example, which publications are incorporated by reference herein for disclosure of those methods and hardware.

The results of such analysis may be compared to results obtained from reference compounds, concentration curves, controls, etc. The comparison of results is accomplished by the use of suitable deduction protocols, AI systems, statistical comparisons, etc.

In particular embodiments, the method described above may be employed in a multiplex assay in which a heterogeneous population of cells is labeled with a plurality of distinguishably labeled binding agents (e.g., a number of different antibodies). After the population of cells is labeled, the cells are introduced into the flow cell, and individually analyzed using the method described above, where the viable cells are distinguished from non-viable cells by the presence of platinum derived from the viability reagent.

A database of analytic information can be compiled. These databases may include results from known cell types, references from the analysis of cells treated under particular conditions, and the like. A data matrix may be generated, where each point of the data matrix corresponds to a readout from a cell, where data for each cell may comprise readouts from multiple mass dot labels. The readout may be a mean, median or the variance or other statistically or mathematically derived value associated with the measurement. The output readout information may be further refined by direct comparison with the corresponding reference readout. The absolute values obtained for each output under identical conditions will display a variability that is inherent in live biological systems and also reflects individual cellular variability as well as the variability inherent between individuals.

Kits

Also provided by the present disclosure are kits for practicing the method as described above. The subject kit contains reagents for performing the method described above, including a viability reagent of the invention, which viability reagent may, in some embodiments, be cisplatin. The platinum content of the reagent may be naturally occurring or synthetically enriched for an isotope of interest. Also included may be buffers, controls, and the like. For example, the kit may also contain a reference sample to which results obtained from a test sample may be compared.

In addition to above-mentioned components, the subject kit may further include instructions for using the components of the kit to practice the methods described herein. The instructions for practicing the subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate. In addition to above-mentioned components, the subject kit may include software to perform comparison of data.

Utility

Exemplary analytic methods employing the above-described method include, for example, antigen identification, disease diagnostics, and the like, particularly methods in which high levels of sensitivity and multiplexing are required; including those methods in which it is desirable to distinguish between living and dead cells.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. All technical and scientific terms used herein have the same meaning as commonly understood to one of ordinary skill in the art to which this invention belongs unless clearly indicated otherwise.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXPERIMENTAL

EXAMPLE 1

A Platinum-Based Covalent Viability Reagent for Single Cell Mass Cytometry

In fluorescence-based flow cytometry, cellular viability is determined with membrane-impermeable fluorescent reagents that specifically enter and label plasma membrane-compromised non-viable cells. A recent technological advance in flow cytometry uses antibodies conjugated to elemental metal isotopes, rather than to fluorophores, to allow signal detection by atomic mass spectrometry. Unhampered by the limitations of overlapping emission fluorescence, mass cytometry increases the number of parameters that can be measured in single cells. However, mass cytometry is unable to take advantage of current fluorescent viability dyes. An alternative methodology was therefore developed here in which the platinum-containing chemotherapy drug cisplatin was used to label cells for mass cytometry determinations of live/dead ratios. In a one-minute incubation step, cisplatin preferentially labeled non-viable cells, from both adherent and suspension cultures, resulting in a platinum signal quantifiable by mass cytometry. This protocol was compatible with established sample processing steps for cytometry. Furthermore, the live/dead ratios were comparable between mass and fluorescence based cytometry. Importantly, although cisplatin is a known DNA-damaging agent, a one-minute "pulse" of cisplatin did not induce observable DNA damage or apoptotic responses even within 6 hours post-exposure. Cisplatin can therefore be used as a viability reagent for a wide range of mass cytometry protocols.

Determination of cellular viability is a critical metric in flow cytometry experiments as it enables the identification and removal of dead cells that could confound functional studies of intracellular signaling, apoptosis, DNA damage, cancer, and drug responses. Fluorescence-based cytometry utilizes a variety of approaches to determine cellular viability status, the most popular of which are "viability dyes". These molecules, including 7-Aminoactinomycin D (7-AAD) and propidium iodide cannot pass through the intact membrane of a live cell, but efficiently enter the cytoplasm and nuclei of dead cells where they intercalate non-covalently into DNA generating a measureable fluorescent signal. Such compounds are effective for discriminating live and dead cells, but are washed out in subsequent cell permeabilization steps needed for well-established intracellular staining protocols.

Covalent protein-reactive fluorescent dyes (e.g., Invitrogen Fixable LIVE/DEAD (Aqua stain)) withstand the formaldehyde crosslinking and permeabilization steps and can be used when many sample processing steps are performed.

Other approaches allow the determination of more specific aspects of apoptotic cell death. Propidium iodide can be used to determine DNA fragmentation occurring during apoptosis, where cells are fixed, permeabilized and treated with RNAse and subsequently stained with propidium iodide. As small DNA fragments generated during apoptosis leak out of the permeabilized cells, the apoptotic cells will yield a lower signal compared to viable cells in the G1, S or G2 phases of the cell cycle. Alternatively, the TdT dUTP nick end labelling (TUNEL) assay can be used to determine DNA fragmentation, where a terminal deoxynucleotidyl transferase labels DNA nicks with fluorescently labeled 2'-deoxyuridine 5'-triphosphate (dUTP), which can be detected by flow cytometry.

Changes in the mitochondrial transmembrane potential, an early hallmark of apoptosis, can be determined by measuring differences in fluorescence of the monomeric and aggregate forms of 5,5',6,6'-tetrachloro-1,1',3,3'tetraethylbenzimidazolylcarbocyanine iodide (JC-1), which exists as both a monomer in the cytosol (green) and as aggregates in the mitochondria (red) in non-apoptotic cells, but remains monomeric in the cytosol of apoptotic cells. Another major class of viability indicators consists of fluorochrome-conjugated antibodies or affinity binders against apopotic specific markers, e.g. against cleaved caspase 3 and cleaved poly-(ADP)-ribose polymerase (PARP) as well as fluorochrome-conjugated Annexin V protein.

Elemental mass spectrometry-based cytometry (mass cytometry) is a recently developed technology platform that characterizes single cells with binding reagents, such as antibodies, aptamers, chemical linkers, or other affinity reagents, in which fluorochromes have been replaced with elemental metal isotopes. Mass cytometry measures the quantity and mass of stable metal isotopes attached to cells via affinity binders, each labeled with polymeric, metal-loaded chelators. The detection modality in mass cytometry is an inductively-coupled plasma mass spectrometer (ICP-MS), which in the current generation of instruments allows for the analysis of spectra encompassing up to 100 isotope channels at an acquisition rate of 1000 cells/second. The high resolution of the time-of-flight (TOF) mass analyzer used in the mass cytometer combined with the intrinsically discrete nature of isotopic masses allows discrimination of isotopes separated by only one atomic mass unit with negligible spectral overlap and dramatically increases the number of parameters that can be measured simultaneously per single cell.

To date, three approaches for determining cell viability by mass cytometry have been described. Ornatsky et al. demonstrated two rhodium- and iridium-containing metallointercalators that were membrane-impermeable. Similar to propidium iodide, these reagents do not form covalent bonds with cellular components, and are thus subject to washout during sample processing. As such, these reagents can only be used as viability dyes when staining is performed shortly before data acquisition. Bendall et al. used an amine-reactive chelator, 1,4,7,10-Tetraazacyclododecane-1,4,7,10-tetraacetic acid mono (N-hydroxysuccinimide ester) (DOTA-NHS-ester) loaded with Rh(III) to label dead cells. This reagent behaves analogously to the amine-reactive fluorescent reagents, but requires same-day preparation in order to produce reproducible results. Majonis et al. described the preferential labeling of dead cells by EDTA polymers loaded with palladium (Pd) or platinum (Pt) ions, conjugated to either antibodies or fluorescein.

Figure 1:
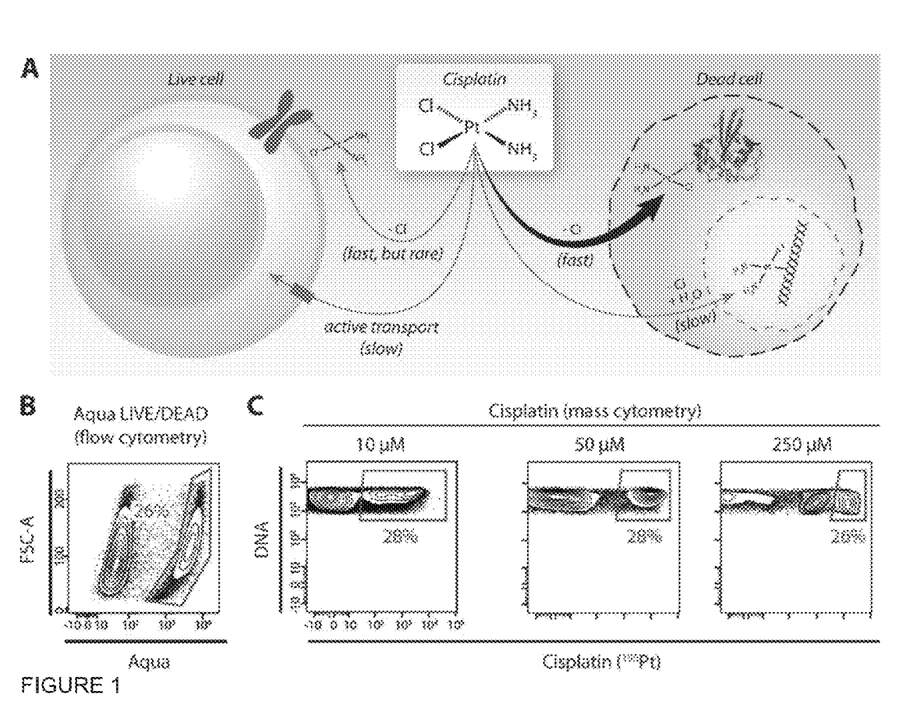
FIG. 1: Cisplatin as a viability reagent for mass cytometry. (A) In a one-minute "pulse" staining protocol, cisplatin preferentially reacts with protein in dead cells. (B) As a basis for comparison, an aliquot of partially heat-killed KG-1 cells was labeled with an amine-reactive fluorescent viability stain (Aqua). (C) Additional aliquots of partially heat-killed KG-1 cells were labeled with cisplatin at the concentrations shown and analyzed by mass cytometry.

Cisplatin [$Pt(NH_3)_2Cl$] is a readily available, platinum-based chemotherapeutic agent, which is used to treat a variety of cancers. After accessing the cell interior, mainly by passive diffusion, cisplatin's cytotoxicity stems from its ability to form 1,2- and 1,3-intrastrand crosslinks between purine bases of DNA, which stalls replication and transcription, resulting in a DNA damage response, cell cycle arrest and ultimately apoptosis. However, these molecular properties were not utilized to measure cell viability. Instead, cisplatin's rapid entrance into a cell with a compromised plasma membrane, followed by its rapid reactivity towards protein nucleophiles such as R—SH or R—S—$CH_3$, with which it can form covalent Pt—S bonds were the features exploited by the viability measurements (FIG. 1A). In a slower, but energetically more favorable process, cisplatin can also become activated by aquation, forming $[Pt(NH_3)_2Cl(OH_2)]^+$ and $[Pt(NH_3)_2(OH_2)_2]^{2+}$, enabling it to form a covalent bond with N7 position of purine bases in DNA (FIG. 1A).

The use of cisplatin to quantitatively discriminate live from dead cells in mass cytometry assays is described herein. Furthermore, the data generated with cisplatin were comparable to those generated with fluorescent viability dyes.

Materials and Methods

Cell culture. The cancer cell lines Jurkat (T acute lymphoblastic leukemia suspension cells) and OVCAR-3 (ovarian carcinoma adherent cells) were cultured in RPMI-1640 (GIBCO, Invitrogen, Carlsbad, Calif.) with 10% heat-inactivated fetal bovine serum (FBS), 2 mM L-glutamine and 100 U/ml penicillin. The suspension cell lines KG-1 (acute myeloid leukemia) and HL-60 (acute myeloid leukemia cells) were cultured in IMDM (GIBCO, Invitrogen, Carlsbad, Calif.) with 20% heat-inactivated FBS and 100 U/ml penicillin. The adherent cell line HeLa (cervical carcinoma) was cultured in DMEM (GIBCO, Invitrogen, Carlsbad, Calif.) with 10% heat-inactivated FBS and 100 U/ml penicillin. All cell lines were maintained at 37° C. in a humidified 5.0% $CO_2$ environment. Peripheral blood from healthy donors was purchased from the Stanford Blood Bank according to an IRB-approved protocol. Peripheral blood mononuclear cells (PBMCs) were separated over Ficoll-Paque Plus (Amersham Biosciences) using Accuspin tubes (Sigma-Aldrich, St. Louis, Mo.) to remove erythrocytes, platelets, and granulocytes. PBMCs were then suspended in FCS with 10% DMSO and frozen at the temperature of liquid nitrogen.

Generation of non-viable control cells. To generate samples with known amounts of non-viable cells, an aliquot of cultured cells was heat-killed at 55° C. for 1 hour, cooled to 37° C. and then spiked into each culture of viable cells at known percentages based on Trypan blue exclusion staining. Samples were then prepared for fluorescence and mass cytometry and the live/dead ratio of cells determined by each technology.

To assess the dynamic range and reproducibility of the viability assay, heat killed HL-60 cells were serially diluted in 2-fold steps and spiked into a cultures with equal amounts of viable HL-60 cells, to generate samples with a final concentration of 40%, 20%, 10%, 5%, 2.5% and 1.25% non-viable cells. Then live/dead cell ratios were determined by Trypan blue exclusion for samples with greater than 5% dead cells. Below this percentage, determining the abundance of dead cells by Trypan blue exclusion is unreliable. Therefore, at low percentages, the number of dead cells was extrapolated based on the serial dilution. Each cell aliquot was divided into triplicates ($2 \times 10^6$ cells/ml), exposed to the cisplatin viability reagent and processed for mass cytometric measurement as described below.

Cisplatin exposure. Cisplatin (WR International, Radnor, Pa., Cat #89150-634) was stored at −80° C. as a stock solution of 100 mM in DMSO (Hybrimax, Sigma Aldrich, St Louis, Mo.). Working solutions (10 mM) were prepared fresh on the day of each experiment by diluting the stock solution into PBS at 4° C. Cells in suspension were centrifuged at 300×g for 5 minutes and resuspended in 1 ml serum-free RPMI at $2 \times 10^6$ cells/ml. The cisplatin working solution was added to cells at a final concentration of 25 µM for 1 min at room temperature, The reaction was quenched with 3 ml of RPMI/10% FBS. Samples were then centrifuged at 300×g for 5 min and cell pellets were resuspended in 1 ml RPMI/10% FBS and processed for cytometry.

Pervanadate stimulation of PBMCs. Frozen PBMCs were thawed at 37° C. and resuspended in RPMI-1640/10% FBS/2 mM EDTA. A fraction of the PBMCs (30%) was heat-killed separately and spiked back in, as described above. Cells were treated with cisplatin according to the standard protocol described above, at $10^6$ cells/ml. Samples were then treated with activated sodium orthovanadate at a final concentration of 125 µM for 15 min at 37° C. Cells were fixed with 1.6% (final concentration) PFA for 10 min at room temperature.

DNA damage response determination. KG-1 cells ($2 \times 10^6$ cells/nil) were exposed to 25 µM cisplatin for 1 min as described above. After quenching, cells were centrifuged at 300×g for 5 min, resuspended at $2 \times 10^6$ cells/mL in RPMI/10% FBS and incubated at 37° C. In order to evaluate whether cisplatin exposure mediated DNA damage, a 1 mL aliquot of cells was removed, fixed in PFA and washed in PBS at times 30 min, 60 min, 120 min, 240 min and 360 min post cisplatin treatment and quenching. Samples were then permeabilized and incubated with antibodies as described.

Antibody staining. After fixation, cells were permeabilized with methanol for 10 min at 4° C., washed twice in cell staining media (CSM; PBS with 0.5% bovine serum albumin and 0.02% sodium azide), and then incubated for 30 min at room temperature simultaneously with relevant antibodies. KG-1 cells were incubated with antibodies against pH2AX and cleaved poly-ADP ribose polymerase (cPARP) to mark cells that had undergone DNA damage and/or apoptosis. PBMCs were incubated with antibodies against surface markers to delineate immune cell subtypes and pSLP-76, an intracellular signaling molecule and substrate for ZAP-70.

For PBMCs treated with pervanadate the antibodies shown in Table 1 were used. For KG-1 cells undergoing DNA damage determination the antibodies shown in table 2 were used. After antibody incubation, cells were washed once in cell staining media (CSM), stained with 1 mL of 1:5000 $^{191/193}$Iridium (Ir) DNA intercalator (DVS Sciences, Richmond Hill, Ontario, Canada), diluted in PBS with 1.6% PFA and incubated for 20 min at room temperature or at 4° C. overnight. Cells were then washed twice with CSM and finally with water for mass cytometric analysis. In order to accurately assess the durability of cisplatin staining in the absence of antibodies, a mock antibody staining procedure was performed with a 30 minute incubation step in 100 µL CSM followed by all subsequent sample processing steps as described above.

TABLE 1

Antibodies used to analyze PMBCs

| ISOTOPE | ANTI-GEN | CLONE | FINAL CONCENTRATION (µg/mL) | SUPPLIER |
|---|---|---|---|---|
| $Pr^{141}$ | CD3 | 145-2C11 | 3 | Invitrogen |
| $Sm^{154}$ | CD45 | HI30 | 2 | Biolegend |
| $Sm^{147}$ | CD20 | H1 | 3 | Biolegend |
| $Gd^{158}$ | CD33 | WM53 | 3 | Biolegend |
| $Gd^{160}$ | pSLP-76 (Y128)/ pSLP-65 (Y72) | J141-668.36.58 | 1 | BD |

TABLE 2

Antibodies used to analyze DNA damage response in KG-1 cells.

| Isotope | Antigen | Clone | Final concentration µM | Vendor |
| --- | --- | --- | --- | --- |
| Nd143 | pH2AX (S139) | JBW301 | 1.2 | Millipore |
| Er167 | cleaved PARP | F21-852 | 1 | BD |

Mass cytometry measurement. Cells were analyzed on a CyTOF® mass cytometer (DVS Sciences, Richmond Hill, Ontario, Canada). The settings of the instrument and the initial post-processing parameters have been described previously (Bendall et al. (2011) Science 332:687-96). Cells were measured at approximately 500 cells per second, noise reduction was activated and cell extraction parameters were set to: Cell length, range was set from 10 to 65 pushes, and the lower convolution threshold was set to 10.

Data analysis and visualization. All cell density plots and histograms shown were created in Cytobank (Cytobank, Inc., Menlo Park, Calif.). After publication all FCS files, including data and time of the experiment, will be made publicly available via Cytobank. All parameters were displayed with an arcsinh transformation, a scale argument of 5, and a display range from −20 to 20,000.

Results

Comparison between fluorescence and mass cytometry protocols. The performance of cisplatin at different concentrations to determine the live/dead cell ratio by mass cytometry was benchmarked against the current standard fluorescent viability stain, Aqua. In the first experiment a suspension of human myeloid KG-1 cells spiked with approximately 30% of heat-killed KG-1 cells (determined by Trypan blue extrusion), was tested with Aqua and cisplatin. The data shown in FIG. 1B verified the ability of Aqua to identify the expected 30% dead cell population.

Cells treated for 1 min with cisplatin showed increased platinum staining with increasing cisplatin concentration (10, 50, or 250 µM), but importantly, showed a comparable frequency (26-28%) of cisplatin positive (dead) cells at all doses. At higher concentrations, the platinum-low (i.e., "live") cell population was labeled with detectable amounts of platinum probably due to non-specific labeling (FIG. 1C, far right hand panel and discussion). The percentages of cisplatin-positive cells were consistent with the percentages of Aqua positive cells (26%) determined from fluorescence cytometry and demonstrated that cisplatin and Aqua were preferentially labeling the same population of dead cells (FIG. 1B, C). These data validate the use of cisplatin as a viability reagent for use in mass cytometry protocols.

Figure 2:
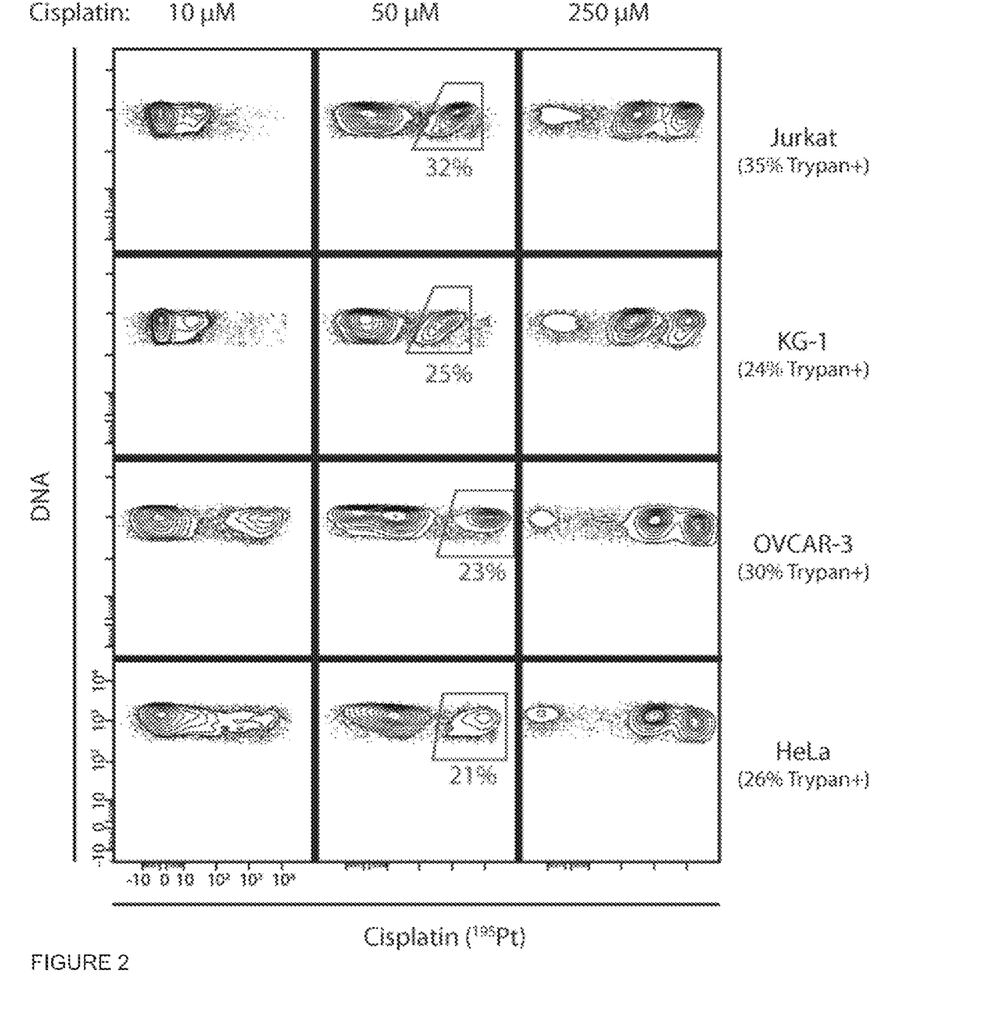
FIG. 2: Cisplatin as a viability indicator for suspension and adherent cell lines. Cisplatin viability labeling was performed at 10, 50 and 250 μM final concentrations for suspension (Jurkat, KG-1) and adherent (HeLa, OVCAR3) cell lines. For all cell lines the percentage of dead cells was comparable as determined by mass cytometry and Trypan blue exclusion.

Adaptability of cisplatin as a viability indicator for suspension and adherent cell lines. In order to determine whether the use of cisplatin could be applied to the mass cytometry workflow for other cell types, it was tested for its ability to recognize live/dead cell ratios in two adherent cell lines; HeLa and OVCAR3 and two suspension cell lines; Jurkat, and KG-1. Suspensions of all cell lines were spiked with a known percentage (as determined by Trypan blue extrusion) of heat-killed cells of the same cell type and the live/dead cell frequencies were measured by mass cytometry of cells exposed to cisplatin at three concentrations (FIG. 2). Distinct cisplatin-high (dead) and cisplatin-low (live) populations were visible at each cisplatin concentration (FIG. 2), with signal-to-noise ratios above 10. The larger, adherent cell lines (OVCAR and HeLa) exhibited higher cisplatin uptake at all concentrations. Indeed, the heat-killed adherent cells acquired so much cisplatin at the highest concentration (250 µM) that the upper limit of the mass cytometer's dynamic range was reached, saturating the signal of the detector and hampering the univocal assignment of viability status at high cisplatin concentrations. These data established an optimal concentration of ~25 µM for viability determinations in cell lines, which was used in all subsequent experiments. These data show that the use of cisplatin for mass cytometry measurements of live/dead ratios is applicable to multiple cell types.

Figure 3:
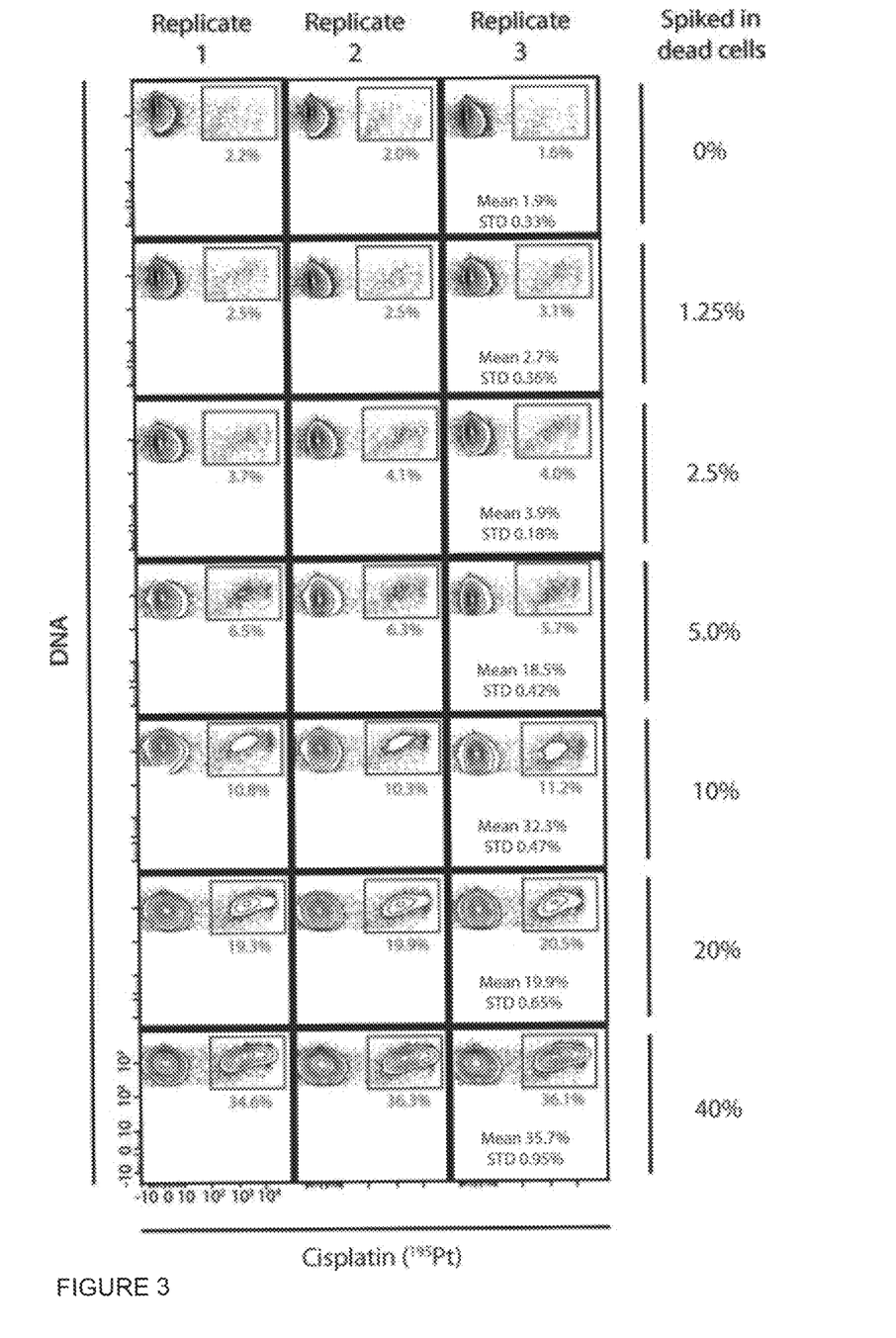
FIG. 3: Reproducibility and dynamic range of the cisplatin viability reagent by mass cytometry. Triplicate samples of HL-60 cells spiked with varying percentages of dead cells ranging from 0-40% were analyzed by mass cytometry using the cisplatin viability reagent. The average percent of dead cells in each sample with their standard deviation are shown. Mass cytometry measurements of cisplatin labeling reproducibly determined the percentage of dead cells over the whole analysis range.

Dynamic range and reproducibility of cisplatin. As with any assay, the application of cisplatin to determine live/dead cell ratios needs to be reproducible and to cover a wide dynamic range. In order to test these parameters, triplicate samples were generated in which a two-fold serial dilution of non-viable HL-60 cells was added to a constant number of viable cells, yielding a titration from 40% to an estimated final concentration of 1.25% (0%) dead cells. These live/dead cell mixtures were then analyzed by the cisplatin viability reagent and mass cytometry. The replicates shown in FIG. 3 establish that mass cytometry of cisplatin-labeled cells reproducibly determined the percentage of dead cells in all samples with standard deviations ranging from 0.18 (sample with 2.5% dead cells) to 0.95 (sample with 40% dead cells) (FIG. 3). The cisplatin assay reliably detected dead cells over the dynamic range of 2.5-40% as analyzed in this experiment. The mass cytometry cisplatin assay was reliable at the upper and lower frequency ranges. Importantly, the assay reproducibly detected low endogenous levels of non-viable cells within the sample, i.e. ~2% dead cells when no heat killed cells were spiked in. This attribute of the assay is essential for determining sample quality in any situation, especially in those measuring intracellular signaling responses in cell subsets within a sample.

Cisplatin as a viability indicator for primary samples. Unlike cell lines, primary samples are mixtures of cell subsets with different sizes and morphologies. To test whether cisplatin can identify dead cells within primary samples, primary PBMCs cryopreserved from a healthy donor with spiked in heat-killed cells were subjected to the cisplatin protocol. In addition, since intracellular signaling responses form an integral part of multiparametric cytometry studies and only occur in viable cells, cisplatin viability measurements were made within the context of signaling. Therefore to evaluate signaling in PBMCs, phosphorylation of SLP-76 (Y128) (T cells and myeloid cells) and SLP-65 (Y76) (B cells) was determined after a 10 minute exposure to vanadate, a global tyrosine phosphatase inhibitor, shown to increase intracellular kinase activity and phosphotyrosine levels.

Figure 4:
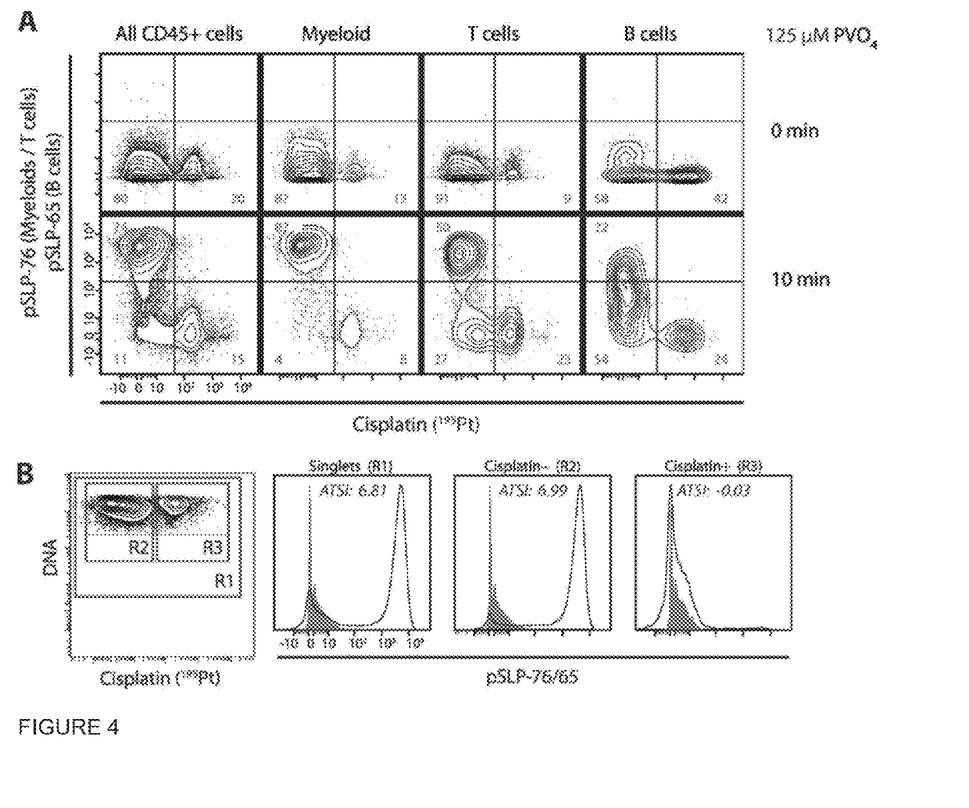
FIG. 4: Cisplatin-high PBMCs were unable to signal in response to pervanadate stimulation. (A) Cryopreserved peripheral blood mononuclear cells were labeled with cisplatin, 25 μM, final concentration for one minute and treated with $PVO_4$, 125 μM, final concentration for 15 minutes. An antibody that cross-reacted with phosphorylated SLP-76 (Tyr128) and SLP-65 (Tyr72) was used as an indicator of intracellular signaling. (B) Histogram overlays shown for pSLP-76/65 in untreated (grey) and vanadate-treated (white) populations. (R1) includes all cells, (R2) only cisplatin low and (R3) only the cisplatin high population.

Distinct cisplatin-low and cisplatin-high populations were seen in populations of myeloid cells, T cells and B cells (FIG. 4A). Furthermore, while cisplatin-low populations of myeloid cells, T cells and B cells showed a strong increase of SLP-76/65 phosphorylation in response to pervanadate, the cisplatin-high populations showed no response (FIG. 4A and FIG. 4B). These data show that cells in which detection of platinum is low are proficient in eliciting a signaling response whereas those where platinum detection is high have lost this proficiency. This validates cisplatin as a viability reagent that can be used to computationally gate or remove dead cells that could confound signaling response data.

Figure 5:
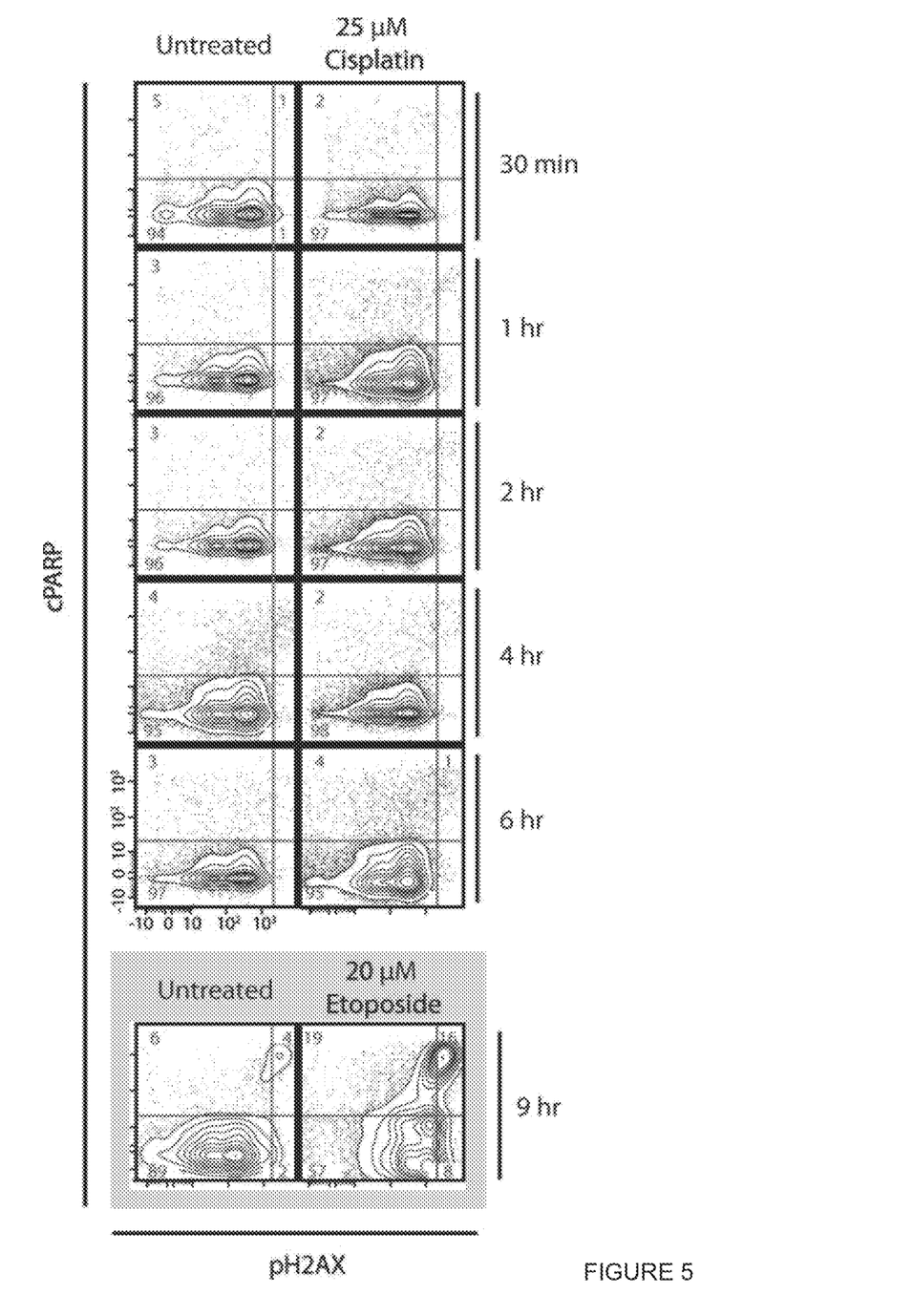
FIG. 5: Cisplatin viability labeling did not induce DDR or apoptosis. When compared with untreated cells, no induction of phosphorylated Ser139 on H2AX (pH2AX) or cleaved PARP (cPARP) was apparent in KG-1 cells incubated for 30, 60, 120, 240 and 360 minutes in cisplatin-free media following a 1-minute "pulse" treatment with cisplatin, 25 μM final concentration. A separate aliquot of cells was treated continuously with 20 μM etoposide for 9 hrs as a positive control for the pH2AX and cPARP antibodies.

Measurement of DNA damage and apoptosis. Cisplatin is used clinically as an anti-cancer agent. Its efficacy is based on its ability to mediate a DNA damage response (DDR) and apoptosis. For all experiments in which a quantitative measurement of viability is necessary, the induction of DDR could preclude the use of cisplatin. To determine whether the cisplatin labeling protocol induces DDR and/or apoptosis, a time course experiment (30 minute-6 hours) was performed for KG-1 cells measuring DDR and apoptosis post a 1 minute pulse of cisplatin. Cells were removed at indicated times, washed and incubated with isotope-tagged antibodies against H2AX (pS139) and cPARP, to measure DDR and apoptosis respectively (FIG. 5). The cisplatin-treated cells showed no increase in H2AX phosphorylation or PARP cleavage up to 6 hours following a one-minute exposure to 25 μM cisplatin (FIG. 5). As a control, KG-1 cells exposed to 20 μM etoposide continuously for 9 hours showed a 4.5 fold increase in the frequency of cPARP+/pH2AX+ cells. These results demonstrate that a rapid cisplatin exposure, for example for 1 minute, does not induce DDR and apoptosis in live cells.

The data reported in this study describe a technically straightforward protocol to measure live/dead ratios in single cells by mass cytometry using commercially available cisplatin. The assay developed is reproducible, has a wide dynamic range, is compatible with many cell types, and allows for routine processing steps necessary to prepare samples for multi-parameter flow cytometry. Critically, the data from fluorescence and mass cytometry were comparable (FIG. 1B and FIG. 1C). The assay data showed that signaling responsiveness, as determined by exposure of cells to vanadate, was severely diminished in cells that were positive for cisplatin staining. Taken together the data describe a means to gate out dead cells which would confound quantification of signaling response and many other types of data.

In order for the cisplatin methodology to be incorporated routinely into mass cytometry protocols, it was evaluated in adherent and suspension cell lines as well as in primary samples. Although the concentration-dependent labeling mechanism resulted in different cisplatin intensities based on cell size, the frequency of cisplatin containing cells within samples of different cell lines was equivalent (FIG. 2). Furthermore, the concentration of cisplatin chosen from the cell line experiments (25 μM), clearly distinguished live from dead cells within different immunophenotypic cell subsets in a primary PBMC sample (FIG. 4).

In comparison to Trypan blue exclusion assays, cisplatin labeling returned slightly lower concentrations of dead cells at high live/dead cells ratios and slightly higher concentrations of dead cells at low live/dead cell ratios (FIG. 3). Likely, two factors are contributing to this outcome. First, as samples are processed for mass cytometry, multiple centrifugation steps preferentially remove dead cells, which are less dense than live cells. This effect is especially pronounced in samples with high percentages of dead cells. Second, the live cell culture used in our serial dilution contained a small percentage of endogenous dead cells (approximately 1.9% by cisplatin staining), which contributed to a greater than expected number of dead cells throughout the serial dilution. Cisplatin/mass cytometry is the method of choice as it measures live/dead ratios simultaneously with other cell parameters.

To maximize the signal-to-noise ratio for the cisplatin assay, a rapid 1-minute "pulse" protocol was developed which allows cisplatin to bind to the abundant reaction sites exposed in a dead cell, while minimizing the amount of time that cisplatin would have to cross the plasma membrane of a live cell. Signal-to-noise ratios of greater than 10-fold separating live and dead cells were routinely observed (FIG. 2-5).

The ability of cisplatin to detect dead cells is due to its access to the cell interior through the compromised plasma membrane, characteristic of dead cells, followed by rapid formation of platinum-sulfur bonds with protein nucleophiles such as R—SH and R—SH—$CH_3$ This is in contrast to cisplatin's covalent reaction with DNA purine residues which take considerably longer to occur (hours) and is associated with cisplatin's cytotoxic effects. By contrast, in live cells cisplatin diffuses slowly across the intact plasma membrane and is minimally detected for the duration of the assay.

The "pulse" method described here did not induce an observable DNA damage response or pro-apoptotic signaling in KG-1 cells 6 hours after the cisplatin pulse (FIG. 5). Compared to other viability reagents currently available for mass cytometry, including the Rh- and Ir-intercalators and Pd/Pt-chelated EDTA polymers, covalent modification of cellular components by cisplatin ensures stability of viability measurements when they are incorporated into cytometry protocols involving multiple rounds of washing and processing (FIG. 5). The stability of cisplatin is particularly useful in cases where cells need to be fixed and frozen for shipment, or for prospective studies.

The generic cisplatin used in the experiments shown here was synthesized from naturally occurring platinum, which contains six stable isotopes (190, 192, 194, 195, 196, 198 A.M.U.). The platinum isotopes occupy mass channels, which, while within the range of the mass analyzer, have not been used by any of the metal-tagged antibodies in previous and ongoing studies. For the data shown in this study, viability determinations were based on measuring only the most abundant isotope ($Pt^{195}$). Synthesis of cisplatin from isotopically enriched platinum would limit the detection spectrum to a single channel, and would allow for an equal signal at lower concentrations of cisplatin while freeing the other platinum channels for additional markers.

The quantification of cisplatin-labeled dead cells developed here for single cell mass cytometry, allows their removal from data analysis of any experimental system. The resultant data generated high quality signal to noise and therefore support incorporating the cisplatin viability determination into mass cytometry protocols.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in chemistry, medicine, and molecular biology or related fields are intended to be within the scope of the following claims.

What is claimed is:

1. A method of distinguishing a viable cell from a dead cell, the method comprising;
    (a) contacting the cell with a viability agent that is a compound that contains platinum where the platinum is non-chelated and the viability agent is in a concentration effective to react with biomacromolecules in a non-viable cell;
    (b) incubating the resultant contacted cell from step (a) for a period of time sufficient to permit entry of the viability reagent into a non-viable cell;

(c) washing the resultant incubated cell from step (b) free of unbound viability reagent; and (d) performing elemental mass spectrometry-based detection to determine if platinum is present in the resultant washed cell from step (c), wherein a non-viable cell is selectively labeled with platinum relative to a viable cell.

2. The method of claim 1, wherein the cell is in a heterogeneous population of cells.

3. The method of claim 1, wherein the platinum content of the viability reagent is a mixture of isotopes.

4. The method of claim 1, wherein the platinum content of the viability reagent is synthetically enriched for an isotope.

5. The method of claim 1, wherein the viability reagent covalently reacts with protein in the cell.

6. The method of claim 1, further comprising analyzing of the cell for additional analytes by elemental or fluorescent detection.

7. The method of claim 1, wherein the cell is fixed and permeabilized following contacting with the viability reagent.

8. A method of distinguishing a viable cell from a dead cell, the method comprising:

(a) contacting the cell with cisplatin at a concentration effective to react with biomacromolecules in a non-viable cell;

(b) incubating the resultant contacted cell from step (a) for a period of time sufficient to permit entry of the cisplatin into a non-viable cell;

(c) washing the resultant incubated cell from step (b) free of unbound cisplatin; and (d) performing elemental mass spectrometry-based detection to determine if platinum is present in the resultant washed cell from step (c), wherein a non-viable cell is selectively labeled with platinum relative to a viable cell.

9. The method of claim 8, wherein the cisplatin is present at a concentration of from about 1 µM to about 250 µM.

10. The method of claim 8, wherein the cisplatin is present at a concentration of from about 10 µM to about 50 µM.

11. The method of claim 8, wherein the incubating step is from about 1 to about 30 minutes.

12. The method of claim 8, wherein the incubating step is from about 1 to about 10 minutes.

13. The method of claim 8, wherein the detection is performed by inductively coupled plasma mass spectrometry, secondary ion mass spectrometry; thermal ionization mass spectrometry, or atomic absorption mass spectrometry.

14. The method of claim 8, wherein the detection is performed by mass cytometry.

* * * * *